United States Patent [19]

Tanabe et al.

[11] Patent Number: 5,214,170
[45] Date of Patent: May 25, 1993

[54] RADIOISOTOPE IODINE-LABELED 1α (OR 24R), 25-DIHYDROXY VITAMIN $D_3$ DERIVATIVES

[75] Inventors: Miyuki Tanabe; Shigeru Ikuta, both of Shizuoka, Japan

[73] Assignee: Toyo Jozo Kabushiki Kaisha, Shizuoka, Japan

[21] Appl. No.: 827,151

[22] Filed: Jan. 27, 1992

Related U.S. Application Data

[62] Division of Ser. No. 417,313, Oct. 5, 1989, Pat. No. 5,117,018.

[30] Foreign Application Priority Data

Oct. 5, 1988 [JP] Japan ................................. 63-251661
Oct. 11, 1988 [JP] Japan ................................. 63-255705

[51] Int. Cl.$^5$ .............................................. C07J 41/00
[52] U.S. Cl. .................................... 552/653; 436/111; 564/394
[58] Field of Search .......................... 552/653; 436/111

[56] References Cited

FOREIGN PATENT DOCUMENTS 55-047653 4/1980 Japan.
58-092656 6/1983 Japan.
58-193463 11/1983 Japan.
59-148775 8/1984 Japan.

OTHER PUBLICATIONS

Nishii et al. "Multiple Assay of Vitamin D and It's Metabolites", *Vitamins*, vol. 55, No. 12, 1981, pp. 595–605.
*Pharma Medica Approach*, vol. 3, No. 1, 1985, pp. 89–96.
*Hormone and Clinical Trials*, vol. 33, No. 10, 1985, pp. 915–924.
Yamamoto, et al. "Monoclonal Antibody for Calcitriol (1α, 25 Dihydroxy-Vitamin $D_3$)" *J. Biochem*, vol. 98, 1985, pp. 991–998.
Eisman et al. "A Sensitive, Precise, and Convenient Method for Determination of 1, 25-Dihydroxyvitamin D in Human Plasma" *Archives of Biochem. and Biophys.*, vol. 176, 1976, pp. 235–243.

(List continued on next page.)

Primary Examiner—Frederick E. Waddell
Assistant Examiner—F. Tsung
Attorney, Agent, or Firm—Young & Thompson

[57] ABSTRACT

A novel 1α (or 24R), 25-dihydroxy vitamin $D_3$ amino acid derivative of the formula

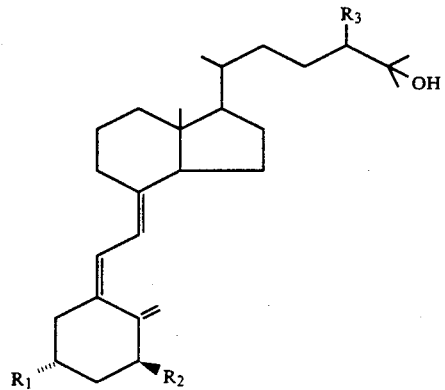

wherein $R_1$ is OH or $-O-CO-A-NH_2$, and $R_2$ and $R_3$ are each selected from the group consisting of hydrogen, OH and $-O-CO-A-NH_2$; wherein one of $R_2$ and $R_3$ is hydrogen, one of R, $R_2$ and $R_3$ is OH, and one of $R_1$, $R_2$ and $R_3$ is $-O-CO-A-NH_2$; and wherein A is $C_{1-10}$ alkylene, is produced by removing a protective group for the amino group, e.g. 9-fluorenylmethyloxycarbonyl, in the presence of a base in an inert solvent. A radioisotope iodine-labeled residue is then attached to the amino group to produce a derivative useful in the assay of 1α (or 24R), 25-dihydroxy vitamin $D_3$ in a specimen.

3 Claims, 2 Drawing Sheets

OTHER PUBLICATIONS

*Clinical Chemistry*, vol. 26, No. 1, 1982, pp. 7–18.
Clemens, et al. "A Radioimmunoassay for 1,25-Dihydroxychol ecalciferol" *Clinical Science and Molecular Medicine*, vol. 54, 1978, pp. 329–332.
Gray, et al., "A Modified Radioimmunoassay for 1,25-Dihydroxycholecalciferol," *Clinical Chemistry*, vol. 27, No. 3, 1981, pp. 458–463.
Bouillon, et al., "A Radioimmunoassay for 1,25-Dihydroxycholecalciferol", *Clinical Chemistry*, vol. 26, No. 5, 1980, pp. 562–567.
Gray, et al., "Radioimmunoassay for 1,25-Dihydroxycholecalciferol", *Clinical Chemistry*, vol. 29, No. 1, 1983, pp. 196–200.
Perry, et al., "Monoclonal Antibody with High Affinity for 1,25-Dihydroxycholecalciferol", *Biochemical and Biophysical Research Com.*, vol. 112, No. 2, 1983, pp. 431–436.

RADIOISOTOPE IODINE-LABELED 1α (OR 24R), 25-DIHYDROXY VITAMIN $D_3$ DERIVATIVES

This application is a division of application Ser. No. 07/417,313, filed Oct. 5, 1989, now U.S. Pat. No. 5,117,018.

FIELD OF THE INVENTION

This invention relates to novel 1α (or 24R), 25-dihydroxy vitamin $D_3$ derivatives, a process for their production, and an assay method using the same.

DESCRIPTION OF THE PRIOR ART

For the assay of 1α, 25-dihydroxy vitamin $D_3$, a radio receptor assay (RRA) method and a radio immunoassay (RIA) method are known. In these methods, a tritium [$^3$H]-labeled compound is used. As the receptor used in the RRA method, it is known to use the receptor from chicken intestine mucosal cytoplasmic fraction [Arch. Biochem. Biophys., 176, 235-243 (1976), *Vitamin*, 55(12), 595-605: 1981, and *Clinical Chem.*, 1(1): 7-18 (1982)]. As haptens for the preparation of antibodies used in the RIA method, substances having carbonyl in a terminal side chain are known. (Japanese Pat. Unexam. Publ. Nos. 58-193463, ibid. No. 58-92656, ibid. No. 55-47653, ibid No. 61-48497 and ibid. No. 59-8775, *Clinical Science and Molecular Medicine*, 54, 329-332 (1978); *Clinical Chem.* 27/3, 458-463 (1981); ibid., 26/5, 562-567 (1980); ibid., 29/1, 196-200 (1983); *J. Biochem.*, 98, 991-998 (1985); *Biochem. Biophys. Res., Comm.*, 431-436 (1983)).

In these assay methods, as the isotopically labeled compound, tritium [$^3$H]labeled 1α, 25-dihydroxy vitamin $D_3$ is used.

In addition, for the assay of 24R, 25-dihydroxy vitamin $D_3$, a competitive protein binding assay (CPBA) method and a HPLC-UV method are known. In the CPBA method, a tritium [$^3$H]-labeled compound is used. As the vitamin D binding protein (DBP) used in the CPBA method, it is also known to use the plasma of rats fed with vitamin D-deficient feed (*Vitamin*, 55 (12), 595-605: 1981, *Pharma Medica*, Vol. 1(1): 89-96 (1985) and *Hormone and Clinical Trials*, Vol. 33, No. 10: 915-924 (1985)).

In the assay of 1α, 25-dihydroxy vitamin $D_3$ in a specimen, the previously used tritium [$^3$H]-labeled compounds were of low specific activity as compared with either of $^{32}$P or $^{125}$I as to radiation energy and suffered from high cost and involved cumbersome operations due to the need for a Liquid Scintillation counter. Moreover, in the assay of 24R, 25-dihydroxy vitamin $D_3$ in a specimen, the HPLC-UV method is less precise and so the CPBA method has been used. However, use of tritium [$^3$H]-labeled compounds in this connection has the same detrimental effects as discussed above.

SUMMARY OF THE INVENTION

We have discovered radioisotope iodine-labeled 1α (or 24R), 25-dihydroxy vitamin $D_3$ derivatives with high radiation energy and superior characteristics of use.

Heretofore, there have been known isotopically labeled vitamin $D_3$ derivatives with tritium [$^3$H]labeling, which have β-ray nuclear emission with low radiation energy per unit time.

However, no information was known on $^{125}$I- or $^{32}$P-labeled vitamin $D_3$ derivatives which have γ-ray nuclear emission with high radiation energy, because the conjugated triene structure of vitamin $D_3$ is unstable and was thought to be subject to auto-degradation by inducing radical reactions.

The $^{125}$I-labeled 1α (or 24R), 25-dihydroxy vitamin $D_3$ derivatives of the present invention are, on the contrary, stable without structural degradation by γ-rays and hence are useful for radio immunoassay.

In radioisotope labeling, direct labeling (chloramin-T method) and indirect labeling (Bolton-Hunter reagent method) are known. (*Amersham Note*, 1 Nov. 1981).

The indirect method under mild reaction conditions is preferable due to the instability of vitamin D in the presence of acid, oxygen, oxidizing agents, heat or light.

We have synthesized novel 1α (or 24R), 25-dihydroxy vitamin $D_3$ amino acid derivatives having a terminal amino group in a side chain. The said derivatives, acting as haptens, are bound with carrier protein and are inoculated into animals to cause formation of antibodies. Furthermore, the derivatives are labeled with radioisotope iodine. Using the obtained antibodies and radioisotope iodine-labeled compounds, we have established a radio immunoassay system, and have found that in an assay of 1α (or 24R), 25-dihydroxy vitamin $D_3$ (hereinafter designated as 1α (or 24R), 25-$(OH)_2$ $D_3$) in a specimen, the assay system according to the invention is highly sensitive and useful.

Moreover, in the CPBA method using DBP, radioisotope iodine-labeled compounds according to the present invention are found to be useful for assaying 1α (or 24R), 25-dihydroxy vitamin $D_3$ with high sensitivity.

OBJECTS OF THE INVENTION

An object of the present invention is to provide novel 1α (or 24R), 25-dihydroxy vitamin $D_3$ amino acid derivatives of the formula [I]

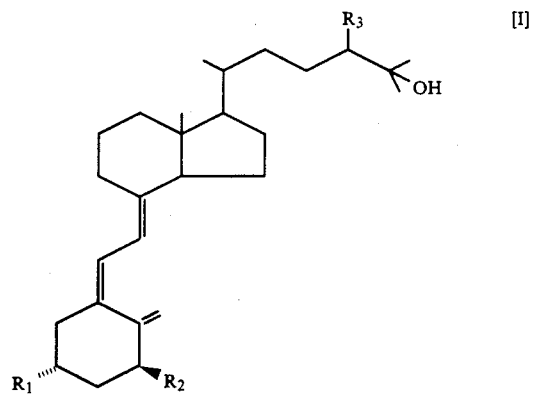

wherein $R_1$ is OH or $-O-CO-A-NH_2$, and $R_2$ and $R_3$ are each selected from the group consisting of hydrogen, OH and $-O-CO-A-NH_2$; wherein one of $R_2$ and $R_3$ is hydrogen, one of $R_1$, $R_2$ and $R_3$ is OH, and one of $R_1$, $R_2$ and $R_3$ is $-O-CO-A-NH_2$; and wherein A is $C_{1-10}$ alkylene.

Another object of the present invention is to provide a process for production of novel 1α (or 24R), 25-dihydroxy vitamin $D_3$ amino acid derivatives [I], which comprises removing a protective group for the amino group in 1α (or 24R), 25-dihydroxy vitamin $D_3$ derivatives of the formula

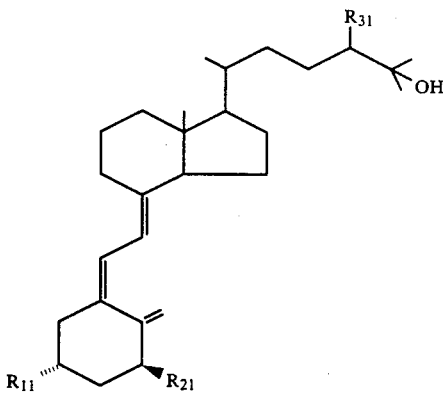

[II]

wherein $R_{11}$ is OH or $-O-CO-A-NH-R_4$, and $R_{21}$ and $R_{31}$ are each selected from the group consisting of hydrogen, OH and $-O-CO-A-NH-R_4$; wherein one of $R_{21}$ and $R_{31}$ is hydrogen, one of $R_{11}$, $R_{21}$ and $R_{31}$ is OH, and one of $R_{11}$, $R_{21}$ and $R_{31}$ is $-O-CO-A-NH-R_4$; and wherein A is $C_{1-10}$ alkylene, and $R_4$ is a protective group for the amino group, in the presence of a base in an inert solvent.

A further object of the present invention is to provide radioisotope iodine-labeled $1\alpha$ (or 24R), 25-dihydroxy vitamin $D_3$ derivatives of the formula

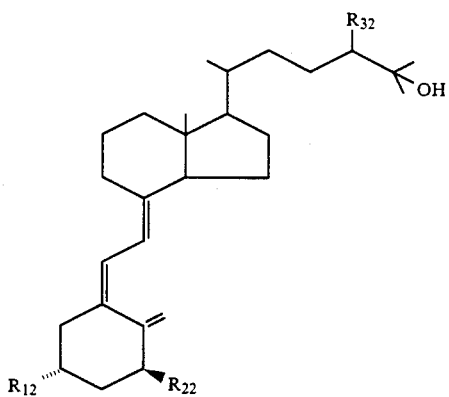

[III]

wherein $R_{12}$ is OH or $O-CO-A-NH-R_5$, and $R_{22}$ and $R_{32}$ are each selected from the group consisting of hydrogen, OH and $-O-CO-A-NH-R_5$; wherein one of $R_{22}$ and $R_{32}$ is hydrogen, one of $R_{12}$, $R_{22}$ and $R_{32}$ is OH, and one of $R_{12}$, $R_{22}$ and $R_{32}$ is $-O-CO-A-NH-R_5$; and wherein A is $C_{1-10}$ alkylene, and $R_5$ is radioisotope iodine-labeled residue.

A still further object of the present invention is to provide an assay method for $1\alpha$ (or 24R), 25-dihydroxy vitamin $D_3$ in a specimen, which comprises the following steps:

adding to a specimen containing $1\alpha$ (or 24R), 25-dihydroxy vitamin $D_3$ a radioisotope iodine-labeled $1\alpha$ (or 24R), 25-dihydroxy vitamin $D_3$ derivative of the formula [III], above;

adding to the mixture thus formed an anti-$1\alpha$ (or 24R), 25-dihydroxy vitamin $D_3$ antibody (hereinafter sometimes designated as antibody) or a vitamin D binding protein (hereinafter designated as DBP);

separating the thus-generated bound form of radioisotope iodine-labeled $1\alpha$ (or 24R), 25-dihydroxy vitamin $D_3$ derivative—anti-$1\alpha$ (or 24R), 25-dihydroxy vitamin $D_3$ antibody or the thus-generated bound form of radioisotope iodine-labeled $1\alpha$ (or 24R), 25-dihydroxy vitamin $D_3$ derivative—DBP from the unreacted free form of radioisotope iodine labeled $1\alpha$ (or 24R), 25-dihydroxy vitamin $D_3$ derivative; and measuring the amount of labeled radioisotope iodine in a bound or free form.

Figure 1:
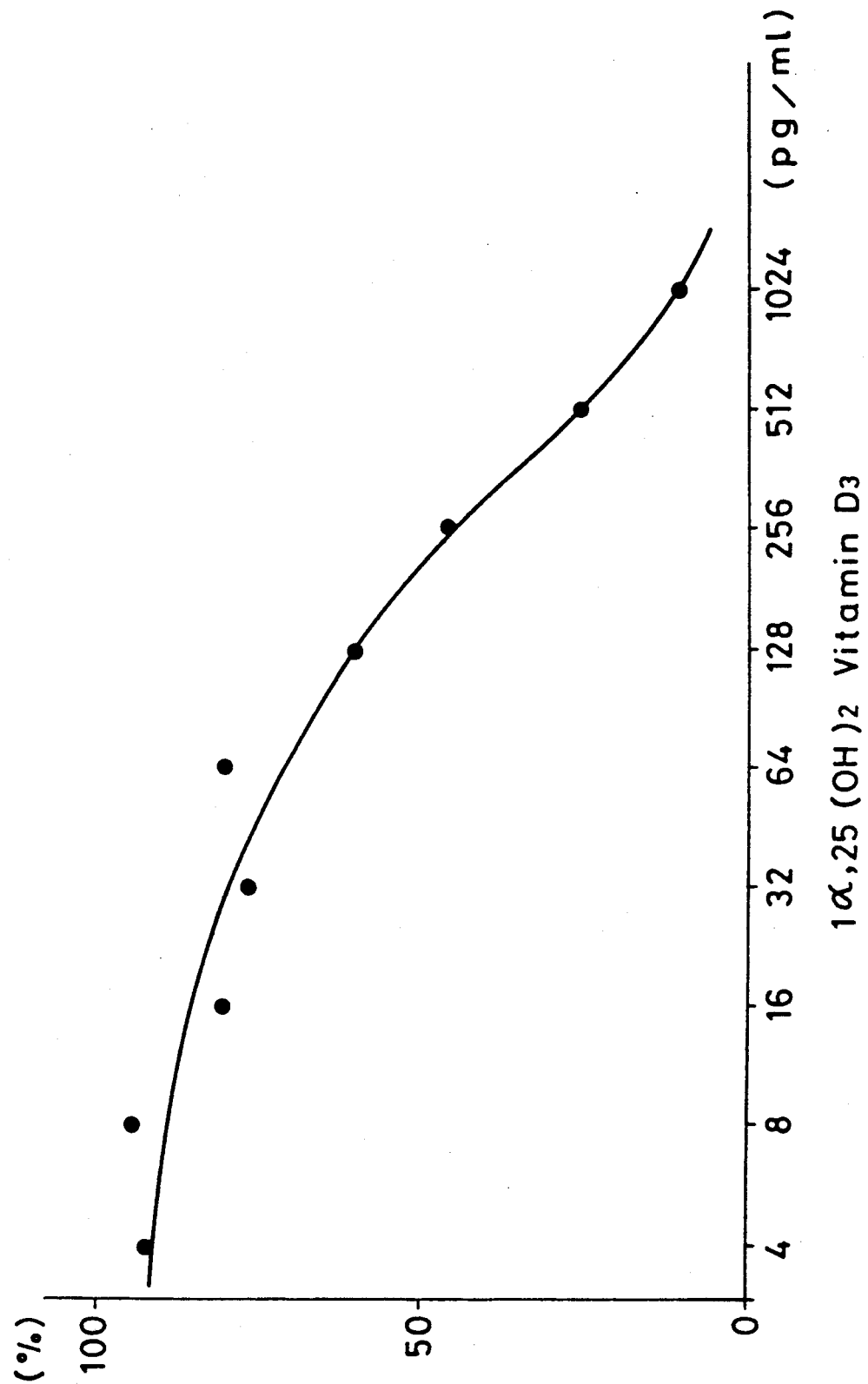
FIG. 1 is the standard curve of $1\alpha$, 25-dihydroxy vitamin $D_3$ using an [$^{125}$I]-labeled $1\alpha$, 25-dihydroxy vitamin $D_3$ derivative.

DETAILED DESCRIPTION OF THE INVENTION $1\alpha$ (or 24R), 25-dihydroxy vitamin $D_3$ amino acid derivatives of formula [I] can be obtained by covalently bonding an amino acid at the $1\alpha$-hydroxy or $3\beta$-hydroxy group of $1\alpha$, 25-dihydroxy vitamin $D_3$, or at the 24R-hydroxy or $3\beta$-hydroxy group of 24R, 25-dihydroxy vitamin $D_3$. In formula [I], A is $C_{1-10}$ alkylene. Compounds of the formula [I] can be used as haptens in the preparation of anti-$1\alpha$ (or 24R), 25-dihydroxy vitamin $D_3$ antibodies. The linkage of such a hapten to a carrier protein is preferably by way of 1-10 carbon chain, and more preferably a 2-6 carbon chain, whereby A is preferably $C_{2-6}$ alkylene.

Compounds of the formula [I] can be prepared by first reacting $1\alpha$ (or 24R), 25-dihydroxy vitamin $D_3$ with an amino acid having a protected amino group to obtain a $1\alpha$ (or 24R), 25-dihydroxy vitamin $D_3$ derivative [II], and then removing the protective group therefrom.

The amino acid is a compound of the formula $$HOOC-A-NH_2 \qquad [IV]$$

wherein A has the same meaning as hereinbefore.

Examples of the amino acid [IV] are: $A=C_1$, glycine; $A=C_2$, $\beta$-alanine; $A=C_3$, $\gamma$-amino-n-butyric acid; A $=C_4$, $\delta$-amino valeric acid; $A=C_5$, $\epsilon$-amino-n-caproic acid; A $=C_6$, 7-amino heptanoic acid; and $A=C_{10}$, 11-amino undecanoic acid. The carbon chain in the amino acid is preferably a straight chain and is preferably $C_{2-6}$ alkylene. $\delta$-amino-levulinic acid, glycylglycine or $\delta$-amino acid, i.e. D and/or L-lysine can also be used. An amino acid having a hydroxy side chain for example 4-amino-3-hydroxybutyric acid, can be used if the hydroxy group is protected.

The protective group for the amino group may be a group which can easily be removed under mild conditions and under weakly basic conditions, due to the possible instability of vitamin D under severe removal conditions. Examples are 9-fluorenyl methyloxycarbonyl (hereinafter designated as Fmoc), 9-(2-sulfo)-fluorenyl methyloxycarbonyl, 1, 1-dimethyl-2-cyanoethyloxy carbonyl and 5-benzisoxazolyl methyloxycarbonyl. 9-fluorenyl methyloxycarbonyl is preferred. Amino group protection can be effected by known methods therefor, for example by reacting an activated derivative, for example an activated ester having Fmoc, such as N-(9-fluorenylmethyloxycarbonyloxy)-succinimide or 9-fluorenylmethylchloroformate, with an amino acid (L. A. Carpino and G. Y. Ham, *J. Org. Chem.* 37: 3404 (1972)).

1α (or 24R), 25-dihydroxy vitamin D₃ amino acid derivatives of formula [II] can be obtained, for example using an Fmoc-amino acid as an amino protected amino acid, by reacting one equivalent of 1α (or 24R), 25-dihydroxy vitamin D₃ with one equivalent of Fmoc-amino acid or its acid anhydride, acid halide or activated ester to obtain compound [II]. The protected amino acid is thereby covalently bound to the 1α-hydroxy or 3β-hydroxy group where 1α, 25-dihydroxy vitamin D₃ is used, and to the 24R-hydroxy or 3β-hydroxy group where 24R, 25-dihydroxy vitamin D₃ is used. More preferably, one equivalent of Fmoc-amino acid is reacted with one equivalent of mixed anhydride having another acid, under an inert gas, and a base in an anhydrous solvent. The reason for reacting the said mixed anhydride with 1α (or 24R), 25-dihydroxy vitamin D₃ is to prevent the formation of a by-product, 1α (or 24R), 25-dihydroxy vitamin D₃ having an Fmocacid on a hydroxy group at position-25.

Examples of other acids in a mixed anhydride are valeric acid, pivalic acid or isobutyloxy carboxylic acid. Pivalic acid is preferred. Examples of anhydrous solvents are anhydrous organic solvents such as dimethylaminopyridine (DMAP) and piperidinopyridine (PPY), which are preferred for the esterification of secondary or tertiary alcohols with steric hindrance. The preferred inert gases are argon and nitrogen. The reaction proceeds preferably at 0°-20 C. for 1-3 hours. The thus-obtained 1α (or 24R), 25-dihydroxy vitamin D₃ derivative [II] is obtained in a mixture in which the group —O—OC—A—NH—R₄ [V], wherein A and R₄ have the same meaning hereinabove, is covalently bound at the 1α or 3β-position of 1α, 25-dihydroxy vitamin D₃ or the 24R- or 3β-position of 24R, 25-dihydroxy vitamin D₃. This compound can be purified, if necessary, by any conventional purification method such as HPLC.

The said 1α (or 24R), 25-dihydroxy vitamin D₃ of formula [II] is subjected to de-protection of the amino group, i.e. removal of Fmoc, in the presence of a base in an inert solvent to produce the corresponding 1α (24R), 25- dihydroxy vitamin D₃ amino acid derivative of the formula [I]. Examples of suitable bases are piperidine, morpholine and ethanolamine. Morpholine is preferred. Examples of suitable inert solvents are ethanol and methanol, preferably anhydrous ethanol and anhydrous methanol. The reaction proceeds under an inert gas, shielded from light, at 0°-20° C. for 1-3 hours.

When the 1α (or 24R), 25-dihydroxy vitamin D₃ derivative [II] is a mixture of compounds in which a residue [V] is covalently bound at the 1α- and 3β-positions of 1α, 25-dihydroxy vitamin D₃, a corresponding product [I] can be isolated and purified from the resulting mixture by HPLC. If the derivative [II] is a previously isolated and purified compound, then the obtained compound can be purified by column chromatography or TLC.

A by-product wherein the residue [V] is covalently bound at the 1α- and 3β-positions of 1α, 25-dihydroxy vitamin D₃ or at the 24R- and 3β-positions of 24R, 25-dihydroxy vitamin D₃, can be reverted back to a starting material, 1α (or 24R), 25-dihydroxy vitamin D₃ by hydrolyzing with dilute aqueous alkali. Alternatively, a compound of the formula [VI]

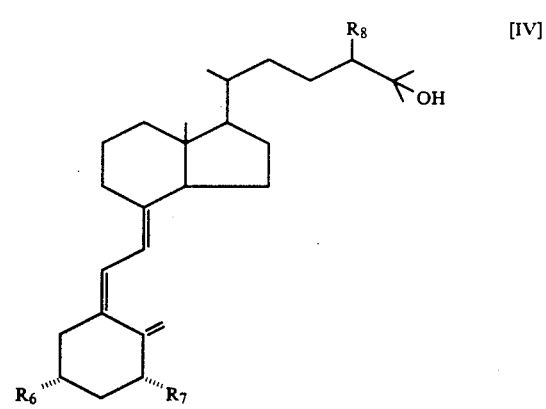

wherein R₆ is —O—CO—A—NH₂, R₇ is hydrogen or —O—CO—A—NH₂, R₈ is hydrogen or —O—CO—A—NH₂, one of R₇ and R₈ is hydrogen and the other is —O—CO—A—NH₂, and A has the same meaning as before, can be obtained by treating such a by-product with morpholine. The compound [VI] is suitable for use as a hapten compound.

In a radioisotope iodine-labeled 1α (or 24R), 25-dihydroxy vitamin D₃ derivative of the formula [III], A has the same meaning as in formula [I] and R₅ is radioisotope iodine-labeled residue. Examples of radioisotopes of iodine are $^{125}I$ or $^{131}I$. The relatively long half life isotope $^{125}I$ is preferred. Examples of radioisotopes of iodine-labeled residues are 3-(4-hydroxy-3-iodo [$^{125}I$]-phenyl)-propionyl, 3-(3, 5-diiodo [$^{125}I$]-4-hydroxyphenyl) propionyl, 2-(4-hydroxy-3-iodo [$^{125}I$] phenyl)acetyl, 2-(3, 5-diiodo [$^{125}I$]-4-hydroxyphenyl) acetyl, 2-iodo [$^{125}I$]acetyl, 4-iodo [$^{125}I$]benzoxymethyl carbonyl and N-substituted-3-iodo [$^{125}I$]tyrosine residue. Among these, 3-(4-hydroxy-3-iodo [$^{125}I$]phenyl) propionyl and 3-(3, 5-diiodo [$^{125}I$]-4-hydroxyphenyl) propionyl are preferred.

In the production of radioisotope iodine-labeled 1α (or 24R), 25-dihydroxy vitamin D₃ derivatives of the formula [III], a 1α (or 24R), 25-dihydroxy vitamin D₃ amino acid derivative of the formula [I] is labeled with radioisotope iodine by an indirect labeling method by means of the Bolton-Hunter reagent to obtain a radicisotope iodine-labeled 1α (or 24R), 25-dihydroxy vitamin D₃ derivative of the formula [III]. An indirect labeling method herein is a method for producing radioisotope iodine-labeled 1α (or 24R), 25-dihydroxy vitamin D₃ derivative of the formula [III] by reacting a reactive derivative of the formula [VII] below, which has a radioisotope iodine-labeled residue, with a 1α (or 24R), 25-dihydroxy vitamin D₃ amino acid derivative of the formula [I].

The above reactive derivative [VII] is expressed by the formula

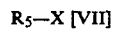    [VII]

wherein R₅ has the same meaning as hereinbefore, and X is succinimidyl-N-oxy, phthalimidyl-N-oxy, 5-norbornene-2, 3-dicarboximidyl-N-oxy or maleimidyl-N-oxy. N-succinimidyl-3-(4-hydroxy-3-iodo [125I]-phenyl)propionate, in which R₅ is 3-(4-hydroxy-3-iodo [125I]phenyl) propionyl and X is succinimidyl-N-oxy in the compound [VII], is a commercially available [$^{125}I$]-Bolton-Hunter reagent. For example, an indirect labeling method of 1α (or 24R), 25-dihydroxy vitamin D₃ amino acid derivative [I] using the said Bolton-Hunter reagent can be conducted by reacting several p moles to several m moles of radioisotope iodine [125I] Bolton-Hunter reagent with a 500–2000-fold excess, preferably a 1000-fold excess, of 1α (or 24R), 25-dihydroxy vitamin D₃ amino acid derivative, at 0°–30° C. for 12–72 hours. In order to increase the effect in the RIO or CPBA method, the produced radioisotope-labeled 1α (or 24R), 25-dihydroxy vitamin D₃ derivative of the formula [III] is preferably purified ty TLC or HPLC. The thus-obtained $^{125}I$-labeled 1α (or 24R), 25-dihydroxy vitamin D₃ derivative is stable at −20° C. in ethanol for longer than the two month half-life of $^{125}I$, and can be used in radio immunoassay.

The storage temperature is preferably as low as possible, e g. 5° C.–−20° C., but is most preferably even below −20° C., in alcohol or ether, under an inert gas.

Anti-1α (or 24R), 25-dihydroxy vitamin D₃ antibodies can be produced by inoculating a conjugation of a hapten, i.e. a 1α (or 24R), 25-dihydroxy vitamin D₃ derivative of the formula [I] and a carrier protein into an animal. Examples of carrier proteins which are essential for obtaining an immunogenic antigen for a hapten, are simple proteins, polypeptides and complex proteins such as glycoproteins. Examples of simple proteins are bovine serum albumin (BSA), human serum albumin or human serum globulin. An example of polypeptide is polylysine. An example of a glycoprotein is mucoprotein. Among these, simple proteins are preferred, and bovine serum albumin and human serum albumin are the most preferred.

1α (or 24R), 25-dihydroxy vitamin D₃ amino acid derivative of the formula [I] and a carrier protein are covalently bonded in the presence of a condensation reagent or crosslinking reagent. Examples of condensation reagents or crosslinking reagents are dicyclohexylcarbodiimide (DCC), acid anhydride and glutaraldehyde. DCC is preferred. The conjugation ratio of the 1α (or 24R), 25-dihydroxy vitamin D₃ amino acid derivative and the carrier protein can be, due to decreasing titer of the antibodies if in excess, 10–40 molecules of 1α (or 24R), 25-dihydroxy vitamin D₃ amino acid derivative per one molecule of carrier protein.

The thus-prepared conjugate for antibody production is inoculated into an animal to produce antibodies. Inoculation can be by parenteral administration such as subcutaneous or intracutaneous injection. For inoculation, a conjugated antigen of the above 1α (or 24R), 25-dihydroxy vitamin D₃ amino acid derivative—carrier protein is dissolved in a buffer solution or physiological saline, together with an equal amount of complete Freund's adjuvant (C.F.A.) The mixture is emulsified completely, and inoculated subcutaneously or intracutaneously into a homeothermal animal, about ten times each 1–3 weeks to immunize the same. Alternatively, the conjugated antigen can be directly inoculated into a spleen. During the immunization period, the serum antibody titer is measured at constant time intervals; and at maximum titer, a whole blood sample is collected and allowed to stand for coagulation. The coagulated sample is centrifugally separated to obtain an antiserum containing anti-1α (or 24R), 25-dihydroxy vitamin D₃ antibodies.

The type of homeothermal animals is not limited and can be any animal which has antibody production activity. To obtain large amounts of antibodies, goat, sheep or bovine can preferably be used. In general, chicken, rabbits, rats or mice are used.

The isolation of anti-1α (or 24R), 25-dihydroxy vitamin D₃ antibody from the antiserum can be performed by any conventional method for antibody purification. For example, ammonium sulfate fractionated antiserum can be treated by ion-exchange chromatography or gel-filtration.

Another method of the production of the antibodies uses spleen cells, which can produce the desired antibodies of the animal, and which are inoculated with conjugated antigen or 1α (or 24R), 25-dihydroxy vitamin D₃ amino acid derivative—carrier protein, and are fused with established myeloma cells, and the thus-obtained hybridoma is cultured. Then the monoclonal antibodies produced by the said hybridoma are used.

For example, an emulsion, which is prepared by mixing a conjugated antigen of 1α (or 24R), 25-dihydroxy vitamin D₃ amino acid derivative—carrier protein dissolved in buffer solution or physiological saline and an equal amount of C.F.A, is inoculated subcutaneously in mice, for example Balb/c for sensitization, with several inoculations each week. Cell-fusion is performed 3–5 days after final sensitization. At 3–5 days after final sensitization, spleen cells which produce anti-1α (or 24R), 25-dihydroxy vitamin D₃ antibodies are collected and fused with established myeloma cells which can be cultured over a long term. Long-term culturable established cells may be defined as cells which can be cultured and growr for a long term in vitro or in vivo, and which can produce immunoglobulin or its related protein. Generally, well-grown myeloma cells are used. Preferred examples of myeloma cells are cell-lines P3-NSI/1-Ag4-1, P3-X63-Ag8Ul, SP2/U-Ag14 and MPCll-45.6.TG.1.7. In the present invertion, P3-X63-Ag8Ul is preferred. The cells can be cultured in a conventional cull culture medium. For example, culturing can be performed in a medium of 10% FCS to which is added RPMI 1640 (trade name, Flow Laboratory) to which is added glutamine, pyruvic acid, penicillin and streptomycin. For stock culture, S-azaguanine is added to the above medium. Myeloma cells, $1-3 \times 10^8$ cells, are used for cell fusion. Spleen cells can be prepared by cutting mouse spleen and crushing it on a mesh to prepare a spleen cell suspension. Washed cells, generally 1 $-3 \times 10^8$ cells, are fused with myeloma cells by mixing together. The ratio of myeloma cells to spleen cells can be 1:3–10. Cell fusion is achieved in a medium for hybridoma. In the cell fusion, a conventional cell-fusion method using a promoter such as Sendai virus or polyethylene glycol (PEG) is preferred. PEG is particularly preferred.

The fused cells are inoculated into the medium for hybridoma and incubated, then selected by incubating in HAT medium. HAT medium is a medium for hybridoma with added hypoxanthine, aminopterin and thymidine. Since more than two hybridomas can be grown in the well of a cell-separation plate, it is possible to produce more than two kinds of antibodies, or no-antibody producing cells may be present as a contaminant; accordingly, in order to obtain cells having the same properties, each clone should be separated. For cloning, a limiting dilution culture or soft agar culture is used. A limiting dilution culture is preferred for use in the invention.

The thus-obtained hybridoma secreting anti-1α (or 24R), 25-dihydroxy vitamin D₃ antibodies with high titer can be stored after lyophilization in an early stage. Lyophilization can be performed by a conventional method, namely cell suspension in a small tube or ampule with freezing in a −80° C. freezer and storage in liquid nitrogen.

Another example of hybridoma production is that the above hybridoma is inoculated intraperitoneally in pristan (2, 6, 10, 14-tetramethylpentadecane, Aldrich Chemicals) treated mice, and after about 10 days the ascites are collected. Another method is that the hybridoma is incubated into bovine fetal serum with added RPMI medium or into Darbecco-modified Eagle medium. The antibodies thus obtained can be purified by any conventional method. For example, the antibodies are fractionated with ammonium sulfate and treated by ion-exchange chromatography, gel filtration and affinity chromatography to fractionate IgG. Then purified anti-1α (or 24R), 25-dihydroxy vitamin $D_3$ monoclonal antibodies can be isolated.

Furthermore, anti-1α (or 24R), 25-dihydroxy vitamin $D_3$ monoclonal antibody-producing cells can be inoculated and grown in an animal having identical histocompatibility antigens or in nude mice as a tumor, and the grown cells collected and the thus-generated monoclonal antibodies separated therefrom.

In an assay of 1α (or 24R), 25-dihydroxy vitamin $D_3$, anti-1α (or 24R), 25-dihydroxy vitamin $D_3$ polyclonal antibodies or anti-1α (or 24R), 25-dihydroxy vitamin $D_3$ monoclonal antibodies (hereinafter sometimes collectively designated anti-1α (or 24R), 25-dihydroxy vitamin $D_3$ antibody) can be used in their soluble state or in an immobilized state. An insoluble carrier and anti-1α (or 24R), 25-dihydroxy vitamin $D_3$ antibodies are bound by using a polyfunctional reagent, and the thus-immobilized antibody has antibody titer against 1α (or 24R), 25-dihydroxy vitamin $D_3$. Examples of polyfunctional reagents are compounds having more than two functional groups which can react with functional groups such as amino, hydroxy, carboxyl and thiol, and comprise aldehydes such as succinaldehyde, glutaraldehyde and adipoaldehyde; dicarboxylates such as malonic acid, succinic acid, glutaric acid, adipic acid and their reactive derivatives; diisocyanates such as hexamethylene diisocyanate and 2,4-toluenediisooyanate; diisothiocyanates such as hexamethylene diisothiocyanate; maleimide carboxylates such as maleimide benzoate, maleimide phenylacetate and their functional derivatives: dimaleimides such as N,N-ethylene-bis-maleimide and N,N'-O-phenylene dimaleimide, bisdiazobenzidine, diethylmalonimidate, dimethyladipinimidate and N,N'-polymethylenebisiodo acetamide, and thiocarboxylates such as 3-(2'-benzothiozolyl-dithio) propionate and 3-(2'-pyridyldithio) propionate or their functional derivatives. The polyfunctional reagent can be selected by considering the bonding of functional groups such as amino, carboxyl, hydroxy or thiol in anti-1α (or 24R), 25-dihydroxy vitamin $D_3$ antibody.

The immobilized carrier is a carrier having a reactive group which does not bond with groups for polyfunctional bonding with antibodies. Examples of immobilized carriers are insoluble proteins such as albumin and gelatin; epichlorhydrin-treated insoluble polysaccharides such as agarose, cellulose and dextrin; insoluble polymers or copolymers of acrylonitrile, acrylic acid, acrylate ester, methacrylic acid, methacrylate ester, vinyl alcohol, vinyl acetate, styrene, aminostyrene, chlorstyrene, maleic acid and fumaric acid, which is treated with bromocyanate and is introduced with a spacer corresponding to amino group introduction, and an insoluble inorganic carrier which is introduced with a functional group such as an amino group into an inorganic compound such as silicon and aluminum. The immobilized carrier may also be a carrier which can bind anti-1α (or 24R), 25-dihydroxy vitamin $D_3$ antibodies by physical adsorption.

The immobilized carrier is preferably in particulate form which can be easily isolated by filtration, for example beads having a diameter more than 1 mm and preferably more than 5 mm, or a spindle form corresponding to the bottom shape of an antigen-antibody reaction tube.

The introduction of a reactive group into anti-1α (or 24R), 25-dihydroxy vitamin $D_3$ antibodies using a spacer-introducing reagent can be performed by introducing additional functional groups such as aldehyde, carboxyl, amino or thiol, reacting with at least one spacer-introducing reagent, for example a dialdehyde such as sur:cinaldehyde, glutaraldehyde or adipoaldehyde; a reactive derivative such as acid chloride, a succinimide ester or p-nitrophenyl ester of ω-amino butyric acid or ω-amino glutamic acid; a reactive derivative of dicarboxylic acids such as malonic acid, succinic acid, glutaric acid or adipic acid; diamines such as hexamethylene diamine or decamethylene diamine; reactive derivatives of 3-(2'-pyridyl-dithio) proponic acid or 3-(2'-benzothiazolyl dithio) propionic acid, S-acetyl-mercapto succinic anhydride or thiols such as 2-aminoethanethiol.

Anti-1α (or 24R), 25-dihydroxy vitamin $D_3$ antibodies are condensed directly or through polyfunctional reagents with reactive groups in the immobilized carrier. Condensation generally proceeds at 0°–40° C. in a pH 6.0–8.5 buffer solution or organic solvent or mixture thereof. Furthermore, a second antibody obtained by immunizing large mammals inoculated with an immunoglobulin fraction in serum, which is used for antibody production of 1α (or 24R), 25-dihydroxy vitamin $D_3$, is immobilized ard anti-1α (or 24R), 25-dihydroxy vitamin $D_3$ antibody is bourd thereto by antigenantibody reaction to prepare the immobilized antibody.

The thus-obtained immobilized antibodies are washed and stored.

In an assay of 1α (or 24R), 25-dihydroxy vitamin $D_3$ in a specimen using anti-1α (or 24R), 25-dihydroxy vitamin $D_3$ antibodies in a liquid soluble phase, a fixed amount of radioisotope iodine-labeled 1α (or 24R), 25-dihydroxy vitamin $D_3$ derivative of the formula [III] is first added to a specimen containing 1α (or 24R), 25-dihydroxy vitamin $D_3$, and then an optimum amount of anti-1α (or 24R), 25-dihydroxy vitamin $D_3$ antibodies is added to form an antigen-antibodies reaction product.

The thus-formed labeled 1α (or 24R), 25-dihydroxy vitamin $D_3$ derivative anti-1α (or 24R), 25-dihydroxy vitamin $D_3$ antibodies binding complex, and the 1α (or 24R), 25-dihydroxy vitamin $D_3$ antibodies binding complex, and the unbound labeled 1α (or 24R), 25-dihydroxy vitamin $D_3$ derivative are separated by using specific antibodies for anti-1α (or 24R), 25-dihydroxy vitamin $D_3$ antibodies. The said specific antibodies are hereinafter referred to as secondary antibodies. The secondary antibodies can be obtained, for example by inoculating a normal immunoglobulin fraction into the serum of an animal which is used for antibodies production of 1α (or 24R), 25-dihydroxy vitamin $D_3$, as an antigen to immunize, then isolating the secondary antibodies from the thus-obtained antiserum. The secondary antibodies can be purified if necessary by any known method, or they can preferably be used in the condition of an antiserum.

An assay method for 1α (or 24R), 25-dihydroxy vitamin D$_3$ in a specimen using anti-1α (or 24R), 25-dihydroxy vitamin D$_3$ antibodies and radioisotope iodine-labeled 1α (or 24R), 25-dihydroxy vitamin D$_3$ derivative is illustrated as follows.

1α (or 24R), 25-dihydroxy vitamin D$_3$ in a specimen such as a known serum, is extracted from the serum specimen. A sample, which is a mixture of serum ard an equal amount of added solvent, is stirred, allowed to stand and centrifuged. The separated supernatant solution is treated by column chromatography and a fraction of 1α (or 24R), 25-dihydroxy vitamin D$_3$ is collected and preferably is purified by HPLC.

The 1α (or 24R), 25-dihydroxy vitamin D$_3$ fraction can be checked by previously added tritium [$^3$H]-labeled 1α (or 24R), 25-dihydroxy vitamin D$_3$. The 1α (or 24R), 25-dihydroxy vitamin D$_3$ fraction is dried in vacuo, flushed with argon gas and dissolved in ethanol to prepare a specimen. A known amount of radioisotope iodine-labeled 1α (or 24R), 25-dihydroxy vitamin D$_3$ derivative is added to a specimen, and the most suitable amount of anti-1α (or 24R), 25-dihydroxy vitamin D$_3$ antibody is added thereto. The mixture is incubated in a medium for antigen-antibodies such as a phosphate buffer or a veronal buffer at 4°-5° C. for about 15-72 hours to promote the competitive reaction of radioisotope iodine-labeled antigen and non-labeled antigen to antibodies. The thus-formed antigen-antibody binding complex, namely a bound form of radioisotope iodine-labeled 1α (or 24R), 25-dihydroxy vitamin D$_3$ derivative anti-1α (or 24R), 25-dihydroxy vitamin D$_3$ antibody (B) and an unreacted free form of radioisotope iodine-labeled 1α (or 24R), 25-dihydroxy vitamin D$_3$ derivative (F) are separated by the dextran-charcoal (DC) method by filtration or by centrifugation at 3,000 r.p.m. for 15 minutes. Upon B-F separation, the radioactivity of each of B and F is measured.

The amount of 1α (or 24R), 25-dihydroxy vitamin D$_3$ (H) in a specimen is determined by expressing the radioactivity of B and F above as B/(B+F) or B/F. Namely, when the amount of H is increased, the radioactivity of B is decreased and that of F is increased. Therefore, the unknown amount of H can be determined by measuring the radioactivity of B and F from a previously plotted standard curve of known amounts.

Upon B-F separation, when the double antibody technique is used with soluble state antibodies, secondary antibodies, preferably secondary antibodies containing an antiserum IgG and if necessary a normal serum IgG of the same kind of animal used for anti-1α (or 24R), 25-dihydroxy vitamin D$_3$ antibodies production, are added after the competitive reaction and incubated for 1-12 hours. Thereafter the formed binding complex is precipitated by centrifugation at 3,000 r.p.m. for 10-30 minutes to separate precipitate (B) and supernatant (F), whereupon the radioactivity of B or F is measured.

According to the present assay method, a standard curve for 2 pg/Test-256 pg/Test can be prepared, and a rapid reaction time of 16 hours at 5° C. or 1 hour at 37° C. can be achieved. Furthermore, the procedure following the reaction is quite simple. Moreover, dilution and recovery tests using the specimens display linearity with high precision.

In addition, when antibodies are replaced by known DBP, it can be reacted with a radioisotope iodine [$^{125}$I]-labeled 1α (or 24R), 25-dihydroxy vitamin D$_3$ derivative and a standard curve for the range 1-32 pg/Test can be prepared. The DBP can be obtained from the serum of chickens, rats, mice, rabbits, goats, sheep, bovines or humans.

The following examples illustrate the present invention but are not to be construed as limiting:

EXAMPLE 1

Extraction and purification of 1α, 25-dihydroxy vitamin D$_3$ is serum

A mixture of 0.5 ml serum and 0.5 ml acetonitrile was stirred in a BORTEX mixer and then allowed to stand for 30 minutes. The supernatant solution (0.8 ml) obtained by centrifugation at 3,000 r.p.m. for 10 minutes was charged on a Sept-pack C-18 cartridge column (tradename, MILLIPORE, Waters Corp.) which was activated with ethanol and equilibrated with 50% acetonitrile, and eluted with hydrated acetonitrile. The column was further washed with 50% acetonitrile (4 ml) then eluted with 64% acetonitrile (4 ml) (to elute a fraction of 1α, 25-dihydroxy vitamin D$_3$), and eluted with 73% acetonitrile (4 ml) (to elute a fraction of 25-dihydroxy vitamin D$_3$ and 24R, 25-dihydroxy vitamin D$_3$). The fraction eluted with 64% acetonitrile was dried in vacuo and flushed with argon gas to obtain a fraction containing 1α, 25-dihydroxy vitamin D$_3$. The thus-obtained crude fraction was dissolved in a 200 μl mixture of 9:1 n-hexane: isopropanol and purified by HPLC in a Zorbax-SIL (Dupont Inc.) 0.46 ×25 cm column. The above fraction of 25-dihydroxy vitamin D$_3$ was checked by previously added tritium [$^3$H]-labeled 1α, 25-dihydroxy vitamin D$_3$[26, 27-methyl-$^3$H]. The fraction of 1α, 25-dihydroxy vitamin D$_3$ (Rt=9-13 minutes) was dried in vacuo and flushed with argon gas.

The resultant fraction was dissolved in ethanol and 10 μl thereof was used for an assay.

The recovery of 1α, 25-dihydroxy vitamin D$_3$ is 95±2% (n=10).

EXAMPLE 2

Preparation of 3-(N-fluorenyl methyloxy carbonyl) amino propionic acid

β-amino-propionic acid (β-alanine, 178 mg, 2 m mole) was added to N-(9-fluorenylmethyloxycarbonyloxy)succinimide (674 mg, 2 m mole) dissolved in a mixture of tetrahydrofuran (THF): dimethylformamide (DMF): H$_2$O (1:2:2) (25 ml) and the mixture was reacted at room temperature overnight. The reaction solvent was distilled off in vacuo and the residue was charged on a column of silica-gel (Wakogel C-200, 75 g) and separated and purified by eluting with CHCl$_3$: methanol (9:1) to obtain the above compound (538.8 mg) (yield: 86.5%).

NMR. δ (DMSO-d6) ppm 2.50-2.60 (2H, t, —CH$_2$—CO—), 3.28-3.35 (2H, m, —CH$_2$—N—), 4.33-4.44 (3H, m, Fmoc), 7.35-8.06 (8H, m, Fmoc).

EXAMPLE 3

Preparation of 1α, 25-dihydroxy vitamin D$_3$-3β-[3-(N-fluorenylmethyloxy carbonyl) aminopropionate] (hereinafter designated as 1α, 25-(OH)$_2$D$_3$-3β-O-Ala-Fmoc) and 1α, 25-dihydroxy vitamin D$_3$-1α-[3-(N-fluorenyl-methyloxy-carbonyl) aminopropionate] (hereinafter designated as 1α, 25-(OH)$_2$D$_3$-1α-O-Ala-Fmoc)

Pivaloyl chloride (trimethyl acetylchloride 3.07 μl, 0.025 m mole) and dimethylamino pyridine (DMAP, 3.05 mg, 0.025 m mole) were added to 3-(N-fluorenyl methyloxy carbonyl) amino propionic acid (Fmoc-β-

Ala, 7.775 mg, 0.025 m mole) dissolved in dry THF (2 ml), and the mixture was reacted at $-15°$ C. for 15 minutes. $1\alpha$, 25-dihydroxy vitamin $D_3$ (10.4 mg, 0.025 m mole) was added thereto and the mixture was reacted at $-15°$ C. for 5 minutes and then at 0° C. for 1.5 hour. Methanol (0.5 ml) was added to the mixture, then distilled off in vacuo. The residue was separated by silica-gel column chromatography (Wako gel C-200, 150 g, developer: ethylacetate: n-hexane (4:1)) to obtain three fractions as follows:

Fraction 1

$1\alpha$, 25-$(OH)_2D_3$-bis($\beta$-Ala-Fmoc), whose full name is $1\alpha$, 25-dihydroxy vitamin $D_3$-$1\alpha$, $3\beta$-bis [3-(N-fluorenyl methyloxy carbonyl) amino] propionate.
Yield: 19.1% (Rf: 0.59)

Fraction 2

A mixture of $1\alpha$, 25-$(OH)_2D_3$-$3\beta$-O-$\beta$-Ala-Fmoc and $1\alpha$, 25-$(OH)_2D_3$-$1\alpha$-O-$\beta$-Ala-Fmoc.
Yield: 20.3% (Rf: 0.47)

Fraction 3

Starting material, $1\alpha$, 25-$(OH)_2D_3$,
Yield: 41.2% (Rf: 0.20)

Fraction 2 was treated with HPLC (Zorbax-ODS; $\phi$ 0.46×25 cm, developer: 10% $H_2O$-methanol; elution: 1 ml/minutes) to separate each component.

The physical properties of each product are shown hereinbelow.

$1\alpha 25$-$(OH)_2D_3$-3-O-$\beta$-Ala-Fmoc:

HPLC Rt=17.46 minutes
NMR. $\delta$ ($CDCl_3$) ppm.
0.55 (3H, s), 0.94 (3H, d), 1.22 (6H, s), 2.53 (2H, t), 3.44–3.48 (3H, m), 4.22 (1H, t), 4.37–4.41 (3H, m), 5.03 (1H, d), 5.27–5.30 (2H, m), 5.35 (1H, m), 6.01 (1H, d), 6.34 (1H, d), 7.29–7.77 (8H, m)
UV$\lambda$max (nm) (EtOH) 300.5, 266.3 214.6.

$1\alpha 25$-$(OH)_2D_3$-$1\alpha$-O-$\beta$-Ala-Fmoc:

HPLC Rt=14.92 minutes.
NMR. $\delta$ ($CDCl_3$) ppm. 0.50 (3H, s), 0.90 (3H, d), 1.20 (3H, s), 1.27 (3H, s), 4.04–4.05 (1H, m), 4.21 (1H, m), 4.41–4.46 (2H, m), 5.05 (1H, d), 5.27 (1H, t), 5.32 (1H, m), 5.50 (1H, t). 5.90 (1H, d), 6.30 (1H, d), 7.28–7.79 (8H, m).
UVmax (nm) (EtOH) 300.4, 266.4, 214.3.

$1\alpha$, 25-$(OH)_2D_3$-bis ($\beta$-Ala-Fmoc):

NMR. $\delta$ ($CDCl_3$) ppm.
0.50 (3H, s), 0.90 (3H, d), 1.20 (3H, s), 1.26 (3H, s), 2.40–2.65 (4H, m), 3.30–3.55 (4H, m), 4.10–4.50 (6H, m), 5.05–5.60 (6H, m), 5.90 (1H, d), 6.32 (1H, d), 7.20–7.83 (16H, m).

EXAMPLE 4

1. Preparation of $1\alpha$, 25-dihydroxy vitamin $D_3$-$3\beta$-O-(3-aminopropionate) (hereinafter designated as $1\alpha$, 25-$(OH)_2D_3$-$3\beta$-O-$\beta$-Ala):

$1\alpha$, 25-$(OH)_2D_3$-$3\beta$-Ala-Fmoc (13.4 mg, 18.86×$10^{-3}$ m mole) was dissolved in ethanol (2.5 ml). Morpholine (2.5 ml) was added thereto and the mixture was stirred at room temperature for 2 hours, under an argon atmosphere. The reaction mixture was concentrated in vacuo to obtain crude product and purified by LH-20 ($H_2O$, 10 ml, tradename) and washed with 20–30 ml water to remove morpholine. The product was eluted with methanol and the thus-eluted product was charged on Amprep-$NH_2$ (Amarsham Corp., 500 mg, n-hexane: dichloromethane 1:1) which was washed with n-hexane: dichloromethane (1:1), 30 ml, then eluted with ethanol to obtain the desired compound.
Yield: 8.73×$10^{-3}$ m mole (46.25%)
UV$\lambda$max (EtOH): 264.2 nm
Ninhydrin colorization: positive.
TLC (Silica-gel, Merck 5715, developer: ethylacetate: methanol=1:4) Rf: 0.15.

2. Preparation of $1\alpha$, 25-dihydroxy vitamin $D_3$-$1\alpha$-O-3-aminopropionate [hereinafter designated as $1\alpha$, 25-$(OH)_2D_3$-$1\alpha$-O-$\beta$-Ala]:

In part 1. of Example 4 above, $1\alpha$, 25-$(OH)_2D_3$-$3\beta$-O-$\beta$-Ala-Fmoc was replaced by $1\alpha$, 25-$(OH)_2D_3$-$1\alpha$-O-$\beta$-Ala-Fmoc to obtain the desired product.
Yield: 62.5%.
UV$\lambda$max (EtOH): 265.4 nm.
Ninhydrin colorization: positive.
TLC (Silica-gel, Merck 5715, ethylacetate-methanol =1:4): Rf: 0.25.

EXAMPLE 5

Preparation of $1\alpha$, 25-dihydroxy vitamin $D_3$-$3\beta$-[3-(BSA-amino) propionate] antigen and $1\alpha$, 25-dihydroxy vitamin $D_3$ antiserum 1. Preparation of $1\alpha$, 25-dihydroxy vitamin $D_3$-$3\beta$-[3-(BSA-amino) propionate] antigen $1\alpha$, 25-$(OH)_2D_3$-$3\beta$-O-$\beta$-Ala (12.2 mg, 25.05×$10^{-3}$ m mole) obtained by removal of Fmoc was dissolved in THF (1 ml), and was added to BSA (M.W. 65,000, 32.6 mg, 1/50×25.05 ×$10^{-3}$ m mole) dissolved in tris buffer (0.1M, pH 8.6, 10 ml) at 0° C. with 1-ethyl-3-(3-dimethylaminopropyl) carbodiimide hydrochloride (6.3 mg, 1.3×25.05×$10^{-3}$ m mole). The reaction mixture was reacted at 0° C. for 3 hours. Chloroform (10 ml) was added four times to the reaction mixture and unreacted $1\alpha$, 25-$(OH)_2D_3$-$3\beta$-O-$\beta$-Ala was removed. The aqueous layer was freeze-dried to obtain the lyophilized product (28.0 mg) which was a complex of 18 molecules of $1\alpha$, 25-$(OH)_2D_3$-$3\beta$-O-$\beta$-Ala bound via an amino group at position 3 thereof to one molecule of BSA.

2. Preparation of $1\alpha$, 25-dihydroxy vitamin $D_3$ antiserum

The lyophilized $1\alpha$, 25-dihydroxy vitamin $D_3$-$3\beta$-[3-(BSA-amino) propionate] (antigen) obtained in part 1. above was dissolved in tris buffer (0.1M, pH 8.6). An equal amount of C.F.A. was added thereto and the material was mixed to emulsify it so as to prepare 1 $\mu$g-100 $\mu$g/ml antigen. The emulsion was inoculated subcutaneously into rabbits ten times each two weeks at a dosage of 10$\gamma$-200 $\gamma$/head. During this immunization, the titer of blood samples collected every ten days was measured ard at maximum antibody titer the whole blood was collected. The blood samples were allowed to stand at room temperature for 60 minutes to coagulate and were then centrifuged at 3,000 r.p.m. for 10 minutes to obtain an antiserum containing anti-$1\alpha$, 25-dihydroxy vitamin $D_3$ antibodies, which was fractionated with ammonium sulfate to collect an IgG fraction.

3. Preparation of anti-1α, 25-dihydroxy vitamin $D_3$ monoclonal antibodies

Lyophilized 1α, 25-dihydroxy vitamin $D_3$-3β-[3-(BSA-amino) propionate] (antigen) obtained in part 1. above, dissolved in phosphate buffer, pH 7.2, (50 γ) together with C.F.A. was inoculated subcutaneously into female Balb/c mice, 4 weeks of age. After 1 week, 50 γ thereof was subcutaneously inoculated and after 2 weeks 50 γ of antigen was intraperitoneally inoculated. Three days after the final inoculation, their spleens were finely cut and crushed on a mesh to prepare a spleen cell suspension. Cell fusion was performed using P3-X63-Ag8U1 mouse myeloma cells, by a conventional method. 30% PEG (M.W. 1,000) aqueous solution was incubated at 37° C. The spleen cells and myeloma cells described (total $4\times 10^7$ cells, 5:1) were suspended in RPMI medium (5 ml) and both types of cells were gently mixed, centrifuged at 1,000 r.p.m. for 10 minutes, whereupon the supernatant was vacuum filtered. The test tube was gently shaken to mix the cell pellets and PEG solution (1.0 ml) was slowly added and the mixture was gently stirred. The mixture was incubated at 37° C. with gentle shaking, then the fusion reaction was stopped by slowly adding a conventional medium (10 ml) and again the cells were suspended. The suspension was centrifuged at 1,000 r.p.m. for 5 minutes. The precipitated cell pellet was dispersed by gently shaking and slowly suspended in HAT medium (5 ml) and was transferred into HAT medium (1 ml) in a vessel. The cells were observed microscopically. The cell suspension was pipetted (each 200 μl) into wells in a 96-well plate and grown in a $CO_2$-incubator. The fused cells were selected in HAT medium for cloning by limiting dilution technique. The obtained clone suspension was grown in the peritonea of pristan-treated Balb/c mice. The IgG fraction was collected by a conventional method from ascites, and serum and purified by affinity chromatography using protein A-bound Sepharose CL-4B. The thus-obtained IgG subclass was IgG 1, and was used as monoclonal antibodies.

EXAMPLE 6

1. Preparation of radioisotope iodine [$^{125}$I]-labeled 1α, 25-dihydroxy vitamin $D_3$ derivative: 1α, 25-dihydroxy vitamin $D_3$-3β-(3-[N-3-(4-hydroxy-3-iodo[$^{125}$I]-phenyl propionyl] amino propionate)

Iodine [$^{125}$I] Bolton-Hunter reagent [NEN, NEX-120-10, 2200 Ci/m mole, 0.33 mCi/100 μl benzene: 50 μCi], THF (75 μl) and triethylamine ($Et_3N$, 300 p mole) were added to an ethanol solution of 1α, 25-$(OH)_2D_3$-3β-O-β-Ala (72 8 n mole/25 μl EtOH) as obtained in Example 5, part 1, and the mixture was reacted at room temperature for 24 hours under an argon atmosphere. The reaction mixture was purified by HPLC.

Radio-recovery: 27.4 μCi (54.7%)

| HPLC: | | |
|---|---|---|
| (1) | Column: | Zorbax-ODS; φ 4.6 × 250 mm 5 μm |
| | Elution: | 15% $H_2O$-methanol, 1 ml/minutes |
| | | Rt: 13.5–15.6 minutes |
| (2) | Column: | Zorbax-SIL; φ 4.6 × 250 mm 5 μm |
| | Elution: | 20% isopropanol-n-hexane; |
| | | 1 ml/minutes: Rt: 16–22 minutes |

2. Preparation of 1α, 25 dihydroxy vitamin $D_3$-1α-(3-[N-3-(4-hydroxy-3-iodine [125I] phenyl) propionylamino]propionate)

In part 1. above, 1α, 25-$(OH)_2D_3$-3β-O-β-Ala was replaced by 1α, 25-$(OH)_2D_3$-1α-O-β-Ala to obtain the desired product.

Radio recovery: 30.2 μCi (60.4%).

| HPLC: | |
|---|---|
| (1) | The same condition as above (1): Rt: 14.2–16.8 minutes |
| (2) | The same condition as above (2): Rt: 13.6–16.1 minutes |

EXAMPLE 7

1. Production of a mixture of 1α, 25-$(OH)_2D_3$-3β-O-β-Ala

Morpholine (2 ml) was added to a mixture (8.4 mg, $\times 10^{-3}$ mole) of 1α, 25-$(OH)_2D_3$-3β-Ala-Fmoc and 1α, 25-$(OH)_2D_3$-1α-O-β-Ala-Fmoc, dissolved in ethanol (2 ml), at room temperature and reacted at room temperature for 2 hours under an argon atmosphere. Reaction solvent was removed in vacuo and the residue was purified by LH-20 ($H_2O$, 10 ml) (Pharmacia Corp.) as in Example 5, part 1.

The residue was further purified by Amprep-$NH_2$ (Amersham Corp., 500 mg) as in Example 5, part 1.

Yield: $5.13 \times 10^{-3}$ m mole (43.4%) [mixture containing approx. 2.5:1 of 1α, 25-$(OH)_2D_3$-3β-O-β-Ala and 1α, 25-$(OH)_2D_3$-1α-O-β-Ala].

UVλmax (EtOH): 265.0 nm.

Ninhydrin colorization: positive.

TLC (Silica-gel, Merck 5715, ethyl acetate-methanol = 1:4): Rf: 0.15 [1α, 25-$(OH)_2D_3$-3β-O-β-Ala], 0.25 [1α, 25-$(OH)_2D_3$-1α-O-β-Ala].

2. Preparation of radioisotope iodine [$^{125}$I]-labeled 1α, 25-dihydroxy vitamin $D_3$-3β-{3-[N-(4-hydroxy-3-iodo [$^{125}$I] phenyl) propionyl] amino propionate} (3β-labeled compound) and 1α, 25-dihydroxy vitamin $D_3$-1α-{3-[N-(4-hydroxy-3-iodo [$^{125}$I] phenyl) propionyl] amino propionate) (1α-labeled compound):

Iodine [$^{125}$I] Bolton-Hunter reagent [NEN, NEX-120-10, 2200 Ci/m mole, 0.33 mCi/100 μl benzene: 100 μCi], THF (30 μl) and triethylamine (600 p mole) were added to an ethanol solution (205 n mole/100 μl ethanol) of the mixture obtained in the part 1 above, and the mixture was reacted at room temperature for 24 hours under an argon atmosphere. The reaction mixture was purified by HPLC.

Radio recovery: 50.7 μCi (50.7%)

| HPLC: | |
|---|---|
| (1) | The same condition as above (1) Rt: 13–17 minutes |
| (2) | The same condition as above (2) Rt: 13–22 minutes |

The 3β-labeled compound and the 1α-labeled compound were separated and purified by HPLC under the condition (2).

| 1α-labeled compound: | Rt: 13.0–15.6 minutes |
| | radio recovery: 16.3 μCi |

| | |
|---|---|
| -continued | |
| 3β-labeled compound: | Rt: 16.0-21.2 minutes<br>radio recovery: 34.5 μCi |

The ratio of recovery of the 1α- and 3β-compounds was 1:2.1, which was identical to the ratio of the starting materials (before de-Fmoc).

EXAMPLE 8

Preparation of standard curve using radio immunoassay of 1α, 25-dihydroxy vitamin $D_3$ A standard ethanol solution of 1α, 25-dihydroxy vitamin $D_3$ was diluted stepwise by two-fold dilution to prepare samples of the following concentration: 1024 pg/20 μl, 512 pg/20 μl, 256 pg/20 μl, 128 pg/20 μl, 64 pg/20 μl, 32 pg/20 μl, 16 pg/20 μl, 8 pg/20 μl and 4 pg/20 μl and 0 (for Bo) and 2048 pg/20 μl (for NSB).

20 μl samples of each of the above concentrations were pipetted into two tubes. 20 μl of an ethanol solution of radioisotope iodine [$^{125}$I]-labeled compound (3β-labeled compound) was pipetted into each tube (20 μl, ca. 12,000 cpm), except samples Bo and NSB.

1 ml of anti-1α, 25-dihydrcxy vitamin $D_3$ sheep serum diluted with tris buffer pH 8.6, was added to each tube. Each mixture in the tubes was incubated at 5° C. overnight, or 16–24 hours. A 200 μl mixture of dextran and activated charcoal, was added to each of the reaction tubes. B-F separation was performed by centrifugation at 5° C. for 30 minutes, and 1 ml of each supernatant solution was measured by using an Autowell γ-counter. The ratio of binding is calculated by the following equation:

$$\text{Binding ratio} = \frac{(B) - (NSB)}{(Bo) - (NSB)} \times 100$$

wherein (B) is the count number in each tube, (NSB) is the count number measured by using 1α, 25-dihydroxy vitamin $D_3$ (2048 pg/200 μl) in place of isotope $^{125}$I labeled 1α, 25-dihydroxy vitamin $D_3$ derivative, and (Bo) is the count number measured by using 1α, 25-dihydroxy vitamin $D_3$ at zero concentration. FIG. 1 shows the standard curve of [125I]-labeled 1α, 25-dihydroxy vitamin $D_3$ derivative as calculated in this manner.

EXAMPLE 9

Extraction and purification cf 24R, 25-dihydroxy vitamin $D_3$ in serum

A mixture of 0.5 ml serum and 0.5 ml acetonitrile was stirred in a BORTEX mixer and then allowed to stand for 30 minutes. The supernatant solution (0.8 ml) obtained by centrifugation at 3,000 r.p.m. for 10 minutes was charged on a Sept-pack C-18 cartridge column (tradename, MILLIPORE, Waters Corp.) which was activated with ethanol and equilibrated with 50% acetonitrile, and eluted with hydrated acetonitrile. The column was further washed with 50% acetonitrile (4 ml) then eluted with 64% acetonitrile (4 ml) (to elute a fraction of 1α, 25-dihydroxy vitamin $D_3$), and eluted with 73% acetonitrile (4 ml) (to elute a fraction of 25-hydroxy vitamin $D_3$ and 24R, 25-dihydroxy-vitamin $D_3$). The fraction eluted with 73% acetonitrile was dried in vacuo and flushed with argon gas to obtain a fraction containing 24R, 25-dihydroxy vitamin $D_3$. The thus-obtained crude fraction was dissolved in a 200 μl mixture of n-hexane: isopropanol (9:1) and purified HPLC in a Zorbax-SIL (Dupont Inc.) 0.46×25 cm column. The above fraction of 24R, 25-dihydroxy vitamin $D_3$ was checked by previously added tritium [$^3$H]-labeled 24R, 25-dihydroxy vitamin $D_3$ [26, 27-methyl-$^3$H]. The fraction of 24R, 25-dihydroxy vitamin $D_3$ (Rt=5–7 minutes) was dried in vacuo and flushed with argon gas.

The resultant fraction was dissolved in ethanol (200 ml) and 20 μl thereof was used for an assay.

The recovery of 24R, 25-dihydroxy vitamin $D_3$ was 2% (n=18).

EXAMPLE 10

Preparation of 24R, 25-dihydroxy vitamin $D_3$-3β-[3-(N-fluorenylmethyloxy carbonyl) aminopropionate] (hereinafter designated as 24R, 25-$(OH)_2D_3$-3β-O-β-Ala-Fmoc) and 24R, 25-dihydroxy vitamin $D_3$-24R-[3-(N-fluorenyl methyloxy carbonyl) aminopropionate] (hereinafter designated as 24R, 25-$(OH)_2D_3$-24R-O-β-Ala-Fmoc)

Pivaloyl chloride (4.62 μl, 1.5×0.025 m mole) and dimethylamino pyridine (DMAP, 4.57 mg, 1.5×0.025 m mole) were added to 3-(N-fluorenyl methyloxy carbonyl) amino propionic acid (hereinafter designated as β-Ala-Fmoc) (11.6 mg, 1.5×0.025 m mole) dissolved in dry THF (2 ml), and the mixture was reacted at −10° C., under an argon atmosphere to produce a mixed anhydride of β-Ala-Fmoc and pivaloyl chloride. The reaction mixture was kept at −10° C. for approximately 10 minutes, and 24R, 25-dihydroxy vitamin $D_3$ (10.4 mg, 0.025 m mole) was added thereto and the mixture was reacted at 0° C. for 30 minutes and then at room temperature for 1 hour. The reaction mixture was concentrated in vacuo after removing a precipitate, then purified by the preparative silica-gel TLC (Merck 5717, 20×20 (H) cm, ethyl acetate: n-hexane=2:1) to obtain the mixture of 24R, 25-$(OH)_2D_3$-3β-O-Ala-Fmoc and 24R, 25-$(OH)_2D_3$-24R-O-β-Ala-Fmoc, a starting material 24R, 25-$(OH)_2D_3$ and 24R, 25-dihydroxy vitamin $D_3$-bis [3-(N-fluorenyl methyloxy carbonyl) amiro] propionate (hereinafter designated as 24R, 25-$(OH)_2D_3$-bis (β-Ala-Fmoc)).

| Yield: | |
|---|---|
| 24R, 25-$(OH)_2D_3$-3β-O-β-Ala-Fmoc | 43.1% |
| 24R, 25-$(OH)_2D_3$-24R-O-β-Ala-Fmoc | 12.7% |
| 24R, 25-$(OH)_2D_3$-bis (β-Ala-Fmoc) | 33.5% |
| recovered starting material 24R, 25-$(OH)_2D_3$ | 10.8% |

Physical properties 24R, 25-$[OH]_2D_3$-3β-Ala-Fmoc

NMR δ (CDCl$_3$) ppm. 0.55 (3H, s), 0.94 (3H, d), 1.17 (3H, s), 1.21 (3H, s), 2.17–2.24 (1H, m), 2.35–2.42 (2H, m), 2.53–2.60 (3H, m), 2.77–2.81 (1H, m), 3.31–3.35 (1H, m), 3.44–3.49 (2H, m), 4.19–4.38 (3H, m), 4.85 (1H, d), 4.98–5.02 (1H, m), 5.07 (1H, m), 5.27–5.30 (1H, b), 6.03 (1H, d), 6.21 (1H, d), 7.29–7.77 (8H, m)

UVλmax (EtOH) (nm) 299.7, 265.2

| HPLC: | |
|---|---|
| (1) | Zorbax-SIL 5% isopropanol-n-hexane,<br>2 ml/minutes, Rt: 14.0 minutes |
| (2) | Zorbax-ODS 10% H$_2$O (CH$_3$CN-methanol = 1:1),<br>2 ml/minutes, Rt: 8.4 minutes |

-continued

| HPLC: |
|---|
| 24R, 25-(OH)$_2$D$_3$-24R-O-$\beta$-Ala-Fmoc: |

NMR δ (CDCl$_3$) ppm.
0.52 (3H, s), 0.92 (3H, d), 1.19 (3H, s), 1.21 (3H, s), 2.15–2.17 (1H, m), 2.25–2.28 (1H, m), 2.30–2.38 (1H, m), 2.55–2.6 (3H, m), 2.79–2.83 (1H, m), 3.48–3.56 (2H, m), 3.93–3.95 (1H, m), 4.20–4.39 (3H, m), 4.80 (1H, d), 4.82–4.85 (1H, m), 5.02 (1H, m), 5.49 (1H, b), 6.01 (1H, d), 6.22 (1H, d), 7.29–7.77 (8H, m).

UVλmax (nm) (EtOH) 299.6, 265.3

| HPLC: | |
|---|---|
| (1) | condition, the same as (1) above, Rt: 18.4 minutes |
| (2) | condition, the same as (2) above, Rt: 6.5 minutes |
| 24R, 25-(OH)$_2$D$_3$-bis ($\beta$-Ala-Fmoc): | |

NMR δ (CDCl$_3$) ppm.
0.52 (3H, s), 0.92 (3H, d), 1.19 (3H, s), 1.21 (3H, s), 2.17–2.22 (1H, m), 2.35–2.41 (2H, m), 2.53–2.61 (5H, m), 2.75–2.78 (1H, m), 3.44–3.57 (4H, m), 4.18–4.39 (6H, m), 4.83–4.85 (2H, m), 4.98–5.01 (1H, m), 5.04 (1H, m), 5.28–5.30 (1H, b), 5.48–5.51 (1H, b), 6.00 (1H, d), 6.20 (1H, d), 7.29–7.77 (16H, m).

EXAMPLE 11

1. Preparation of 24R, 25-dihydroxy vitamin D$_3$-3$\beta$-(3-aminopropionate) (hereinafter designated as 24R, 25-(OH)$_2$D$_3$-3$\beta$-O-$\beta$-Ala)

24R, 25-(OH)$_2$D$_3$-3$\beta$-O-$\beta$-Ala-Fmoc (2.4 mg, 3.38×10$^{-3}$ m mole) as produced in Example 10 was dissolved in ethanol (1 ml). Morpholine (1 ml) was added thereto and the mixture was reacted at room temperature for two hours. The reaction mixture was concentrated in vacuo and purified by LH-20 (H$_2$O ml, tradename) and then washed with 30 ml purified water to remove morpholine. The product was eluted with methanol and the thus-eluted product was concentrated and charged on Amprep-NH$_2$ (Amersham Corp., 500 mg, n-hexanedichloromethane 1:1) which was washed with 20 ml n-hexane: dichloromethane (1:1), 20 ml, then eluted with ethanol to obtain the desired compound.
Yield: 25.4%.
UVλmax (EtOH): 264.6 nm.
Ninhydrin colorization: positive.

2. Preparation of 24R, 25-dihydroxy vitamin D$_3$-24R-O-$\beta$3-aminopropionate (hereinafter designated as 24R, 25-(OH)$_2$D$_3$-24R-O-$\beta$-Ala)

In part 1 above, 24R, 25-(OH)2D$_3$-3$\beta$-O-$\beta$-Ala-Fmoc was replaced by 24R, 25-(OH)$_2$D$_3$-24R-O-$\beta$-Ala-Fmoc to obtain the desired product.
Yield: 40%.
UVλmax (EtOH): 265.4 nm.
Ninhydrin colorization: positive.

EXAMPLE 12

1. Preparation of radioisotope iodine [$^{125}$I]-labeled 24R, 25-dihydroxy vitamin D$_3$ derivative: 24R, 25-dihydroxy vitamin D$_3$-3$\beta$-{3-[N-(4-hydroxy-3-iodo [$^{125}$I]phenyl) propionyl] amino propionate)

Iodine [$^{125}$I] Bolton-Hunter reagent [NEN, NEX-120-10, 2200 Ci/m mole] (50 μCi/30 pM/15 μl benzene), THF (20 μl) and triethylamine 300 p mole) were added to an ethanol solution of 24R, 25-(OH)$_2$D$_3$-3$\beta$-O-$\beta$-Ala (66.35 n mole/100 μl EtOH) as obtained in part 1 of Example 11 and the mixture was reacted at room temperature for 24 hours under an argon atmosphere, shielded from light. The reaction mixture was purified by HPLC.

| HPLC: | | |
|---|---|---|
| (1) | Zorbax-ODS; | 15% H$_2$O-methanol, 1 ml/minutes Rt: 12.0–13.3 minutes |
| (2) | Zorbax-SIL; | 20% isopropanol-n-hexane, 1 ml/minutes, Rt: 12.6–17.2 minutes |

Radio-recovery: 29.9 μCi (59.7%)

2. Preparation of 24R, 25-dihydroxy vitamin D$_3$-24R-O-[3-{N-3-(4-hydroxy-3-iodine [$^{125}$I] phenyl) propionylamino) propionate In part 1 above, 24R, 25-(OH)$_2$D$_3$-3$\beta$-O-$\beta$-Ala was replaced by 24R, 25-(OH)$_2$D$_3$-24R-O-$\beta$-Ala as obtained in part 2 of Example 11, to obtain the desired product.

| HPLC: | |
|---|---|
| (1) | Conditions, the same as (1) above: Rt: 9.9–11.3 minutes |
| (2) | Conditions, the same as (2) above: Rt: 11.3–14.8 minutes |

Radio-recovery: 53.9%.

EXAMPLE 13

Preparation of standard curve of 24R, 25-(OH)$_2$D$_3$ using radioisotope iodine [$^{125}$I]-labeled 24R, 25-(OH)$_2$D$_3$ A standard ethanol solution of 24R, 25-(OH)$_2$D$_3$ (1.024 pg/20 μl) was diluted stepwise by two-fold dilutions to prepare samples of the following concentration: 128 pg/20 μl, 64 pg/20 μl, 32 pg/20 μl, 16 pg/20 μl, 8 pg/20 μl, 4 pg/20 μl, 2 pg/20 μl, and 0 pg/20 μl.

20 μl samples of each of the above concentrations were pipetted into two tubes. 20 μl aliquots of an ethanol solution of radioisotope iodine [$^{125}$I]-labeled 24R, 25-(OH)$_2$D$_3$ derivative, containing as an antioxidant tocopherol, were pipetted into each tube (20 μl, ca. 13,000 cpm). 1 ml of DBP diluted with tris buffer, pH 8.6, was stirred into each of the tubes, which were then allowed to stand at 5° C. overnight (20–24 hours).

Figure 2:
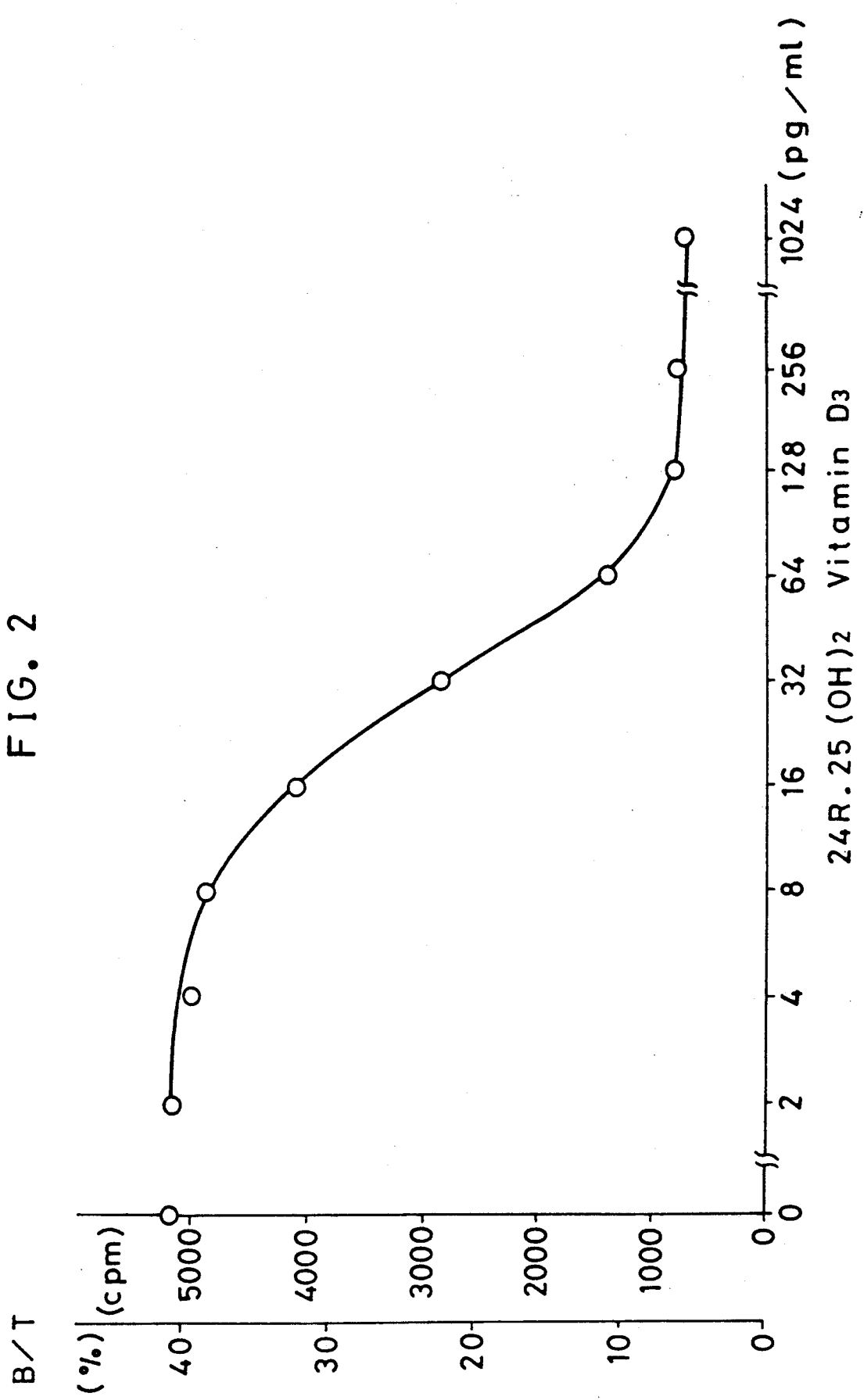
FIG. 2 is the standard curve of 24R, 25-dihydroxy vitamin $D_3$ using an [$^{125}$I]-labeled 24R, 25-dihydroxy vitamin $D_3$ derivative.

200 μl of a solution of dextran and activated charcoal was added to each of the reaction tubes, stirred and incubated at 5° C. for 30 minutes, with stirring at 15 minute intervals. B-F separation was performed by centrifugation at 3,000 r.p.m. for 15 minutes, and 1 ml of each supernatant solution was measured by using an Autowell γ-counter. The standard curve can be prepared by plotting an average count obtained in each tube. The results are shown in FIG. 2.

It will thus be seen that the present invention provides radioisotope iodine-labeled 1α, 25-dihydroxy vitamin D$_3$ derivatives with high radiation energy and wide usability, compared to low radiation energy, β-ray emitting tritium [$^3$H]-labeled vitamin D$_3$. It might be thought that high radiation energy radioisotope iodine [$^{125}$I] or phosphorus [$^{32}$P] vitamin D$_3$ would degrade automatically due to reaction of the conjugated double bond in the vitamin D structure. But it has been found that [$^{125}$I]-labeled 1α (or 24R), 25-dihydroxy vitamin D₃ derivatives according to the present invention in fact do not autodegrade by the action of γ-rays, and are quite stable for use in radio immunoassay.

In general, vitamin D₃ is metabolized in vivo in the liver and kidney and is converted to activated vitamin D₃. The activated vitamin D₃, such as 25-hydroxy vitamin D₃, 1α, 25-dihydroxy vitamin D₃, 1α-hydroxy, vitamin D₃ and 1α, 24-dihydroxy vitamin D₃, is used clinically for the therapeutic treatment of osteoporosis and osteomalacia. The clinical dosages thereof are quite low due to their strong physiological action. The pharmacological activity is correlated to the blood level and tissue level of the drug and hence measurement of the blood level of the drug administered to humans is important from a clinical point of view. Considering the above, the present invention is valuable for the assay of activated vitamin D₃ in clinical tests.

Although the present invention has been described in connection with various preferred embodiments thereof, it will be appreciated that these embodiments are provided solely for purposes of illustration, and should not be construed as limiting the scope of the invention. Other embodiments and applications of the invention will be readily apparent to those skilled in the art from reading the present specification and practicing the techniques described herein, without departing whatsoever from the scope and spirit of the appended claims.

What is claimed is:

1. A radioisotope iodine-labeled vitamin D₃ derivative of the formula

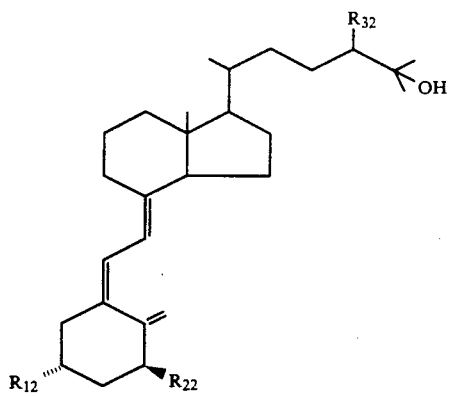

wherein $R_{12}$ OH or —O—CO—A—NH—$R_5$, and $R_{22}$ and $R_{32}$ are each selected from the group consisting of hydrogen, OH and —O—CO—A—NH—$R_5$; wherein one of $R_{22}$ and $R_{32}$ is hydrogen, one of $R_{12}$, $R_{22}$ and $R_{32}$ is OH, and one of $R_{12}$, $R_{22}$ and $R_{32}$ is —O—CO—A—NH—$R_5$; and wherein A is $C_{1-10}$ alkylene, and $R_5$ is radioisotope iodine-labeled residue.

2. A radioisotope iodine-labeled vitamin D₃ derivative according to claim 1 wherein the radioisotope iodine is $^{125}$I.

3. A radioisotope iodine-labeled vitamin D₃ derivative according to claim 1 wherein the radioisotope iodine-labeled residue is 3-(4-hydroxy-3-iodo [$^{125}$I]-phenylpropionyl or 3-(3,5-diiodo-[$^{125}$I]-4-hydroxyphenyl)-propionyl.

* * * * *